United States Patent [19]

Hester, Jr.

[11] 4,082,761
[45] * Apr. 4, 1978

[54] TRIAZOLO[4,3-a][1,4]BENZODIAZEPINIUM QUATERNARY SALTS

[75] Inventor: Jackson B. Hester, Jr., Galesburg, Mich.

[73] Assignee: The Upjohn Company, Kalamazoo, Mich.

[*] Notice: The portion of the term of this patent subsequent to Aug. 7, 1990, has been disclaimed.

[21] Appl. No.: 393,940

[22] Filed: Sep. 4, 1973

[51] Int. Cl.² .......................................... C07D 487/04
[52] U.S. Cl. ......................... 260/308 R; 260/239 BD; 260/239.3 D; 424/244; 424/269
[58] Field of Search ..................... 260/239 BD, 308 R

[56] References Cited

U.S. PATENT DOCUMENTS 3,696,094  10/1972  Tachikawa et al. ........... 260/239.3 D
3,751,426  8/1973   Hester .............................. 260/308 R

FOREIGN PATENT DOCUMENTS 2,012,190  9/1970  Germany .......................... 260/308 R

*Primary Examiner*—Alton D. Rollins
*Attorney, Agent, or Firm*—John T. Reynolds; William A. Hodes

[57] ABSTRACT

This invention relates to novel benzodiazepinium compounds of the formula

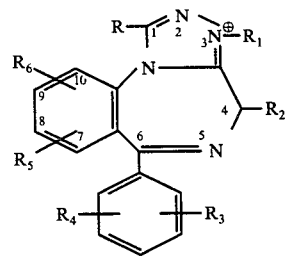

XIII (VI through VIII)

wherein R is selected from the group consisting of hydrogen, lower alkyl of 1 through 3 carbon atoms, hydroxy, mercapto, amino, monoalkylamino of 1 through 3 carbon atoms, arylamino wherein the aryl moiety is selected from the group consisting of unsubstituted and monosubstituted phenyl and naphthyl, alkanoylamino of 1 through 4 carbon atoms, aroylamino wherein the aroyl moiety is selected from the group consisting of unsubstituted and monosubstituted benzoyl and naphthoyl, alkanesulfonamido of 1 through 3 carbon atoms, and arylsulfonamido wherein the aryl moiety is selected from the group consisting of unsubstituted and monosubstituted phenyl and naphthyl; $R_1$ is lower alkyl of 1 through 3 carbon atoms; $R_2$ is selected from the group consisting of hydrogen and lower alkyl of 1 through 3 carbon atoms; $R_3$, $R_4$, $R_5$ and $R_6$ are selected from the group consisting of hydrogen, lower alkyl of 1 through 3 carbon atoms, halogen, nitro, trifluoromethyl, cyano, lower alkoxy of 1 through 3 carbon atoms and lower alkylthio of 1 through 3 carbon atoms; $X^\ominus$ is an anion derived from a pharmacologically acceptable acid addition salt; $\oplus$ is the cation of the compound. The new compounds of Formulae VI, VII, VIII, IX, X and XI, set forth below, are included within generic Formula XIII, above. The invention also relates to inner salt compounds of the formula

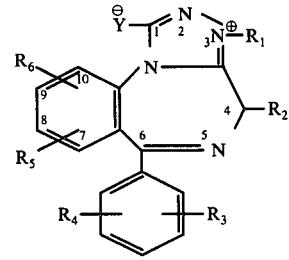

IV, V, IX, X, XI wherein Y is selected from the group consisting of hydroxy, mercapto and monosubstituted amino having an electronegative substituent selected from the group consisting of arylamino, alkanoylamino, aroylamino, alkanesulfonamide and arylsulfonamide, said terms, as well as $R_1$, $R_2$, $R_3$, $R_4$, $R_5$, $R_6$ and $\oplus$, having the same meaning as above, and $\ominus$ appearing above Y indicates that the compound is an inner salt. The invention also includes novel intermediates (III) for the production of the novel compounds of Formulae IV through XI having the formula

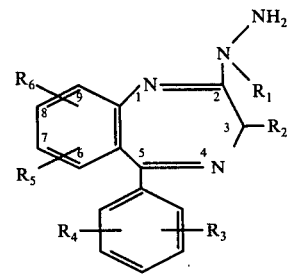

III wherein $R_1$, $R_2$, $R_3$, $R_4$, $R_5$ and $R_6$ have the same meaning as above. It further relates to novel compounds (XII) prepared from those of Formula VII (wherein R' is hydrogen) and having the formula

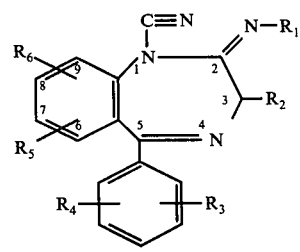

XII wherein $R_1$, $R_2$, $R_3$, $R_4$, $R_5$ and $R_6$ have the same meaning as above. It also relates to processes for the preparation of the novel compounds of Formulae II through XII. The systemic administration to humans and animals of the new products of Formulae IV through XII depresses their central nervous systems.

17 Claims, No Drawings

TRIAZOLO[4,3-a][1,4]BENZODIAZEPINIUM QUATERNARY SALTS

BRIEF SUMMARY OF THE INVENTION

This invention relates to new organic compounds and is particularly concerned with those embraced by the formula

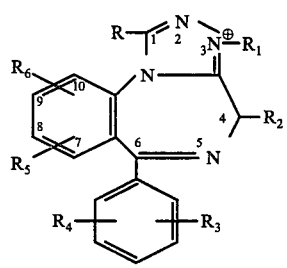

XIII (VI through VIII)

wherein R is selected from the group consisting of hydrogen, lower alkyl of 1 through 3 carbon atoms, hydroxy, mercapto, amino, monoalkylamino of 1 through 3 carbon atoms, arylamino wherein the aryl moiety is selected from the group consisting of unsubstituted and monosubstituted phenyl and naphthyl, alkanoylamino of 2 through 4 carbon atoms, aroylamino wherein the aroyl moiety is selected from the group consisting of unsubstituted and monosubstituted benzoyl and naphthoyl, alkanesulfonamido of 1 through 3 carbon atoms, and arylsulfonamido wherein the aryl moiety is selected from the group consisting of unsubstituted and monosubstituted phenyl and naphthyl; $R_1$ is lower alkyl of 1 through 3 carbon atoms; $R_2$ is selected from the group consisting of hydrogen and lower alkyl of 1 through 3 carbon atoms; $R_3$, $R_4$, $R_5$ and $R_6$ are selected from the group consisting of hydrogen, lower alkyl of 1 through 3 carbon atoms, halogen, nitro, trifluoromethyl, cyano, lower alkoxy of 1 through 3 carbon atoms and lower alkylthio of 1 through 3 carbon atoms; $X^\ominus$ is an anion derived from a pharmacologically acceptable acid addition salt; $\oplus$ is the cation of the compound. The new compounds of Formulae VI, VII and VIII set forth below, are included within generic Formula XIII, above. The invention also covers inner salt compounds of the formula

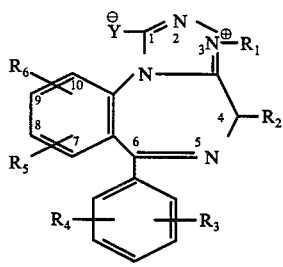

IV, V, IX, X, XI wherein Y is selected from the group consisting of hydroxy, mercapto and monosubstituted amino having an electronegative substituent selected from the group consisting of arylamino, alkanoylamino, aroylamino, alkanesulfonamido and arylsulfonamido, said terms, as well as $R_1$, $R_2$, $R_3$, $R_4$, $R_5$, $R_6$ and $\oplus$, having the same meaning as above, and $\ominus$ appearing above Y indicates that the compound is an inner salt. The invention also includes novel intermediates (III) for the production of the novel compounds of Formulae IV through XI and having the formula

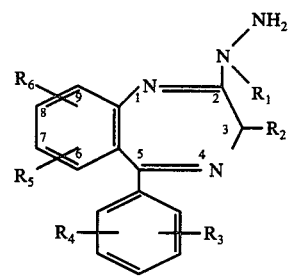

III wherein $R_1$, $R_2$, $R_3$, $R_4$, $R_5$ and $R_6$ have the same meaning as above, and novel compounds (XII) prepared from those of Formula VII (wherein R' is hydrogen) and having the formula

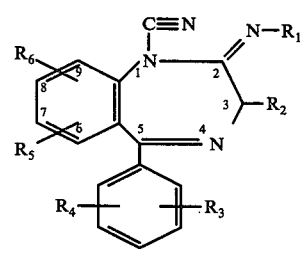

XII wherein $R_1$, $R_2$, $R_3$, $R_4$, $R_5$ and $R_6$ have the same meaning as above.

Examples of monoalkylamino of 1 through 3 carbon atoms include methylamino, ethylamino, propylamino and isopropylamino. Examples of arylamino having aryl moieties of unsubstituted and monosubstituted phenyl and naphthyl include phenylamino, o-, m- and p-tolylamino, 2-naphthylamino and 3-methylnaphthylamino. Examples of alkanoylamino of 2 through 4 carbon atoms include acetylamino, propionylamino and butyrylamino. Examples of aroylamino having aroyl moieties of unsubstituted and monosubstituted benzoyl and naphthyl include benzoylamino, o-, m- and p-tolylamino, 3-naphthoylamino and 5-methyl-1-naphthoylamino. Examples of alkanesulfonamido of 1 through 3 carbon atoms include methanesulfonamido, ethanesulfonamido, propanesulfonamido and isopropanesulfonamido. Examples of arylsulfonamido having aryl moieties of unsubstituted and monosubstituted phenyl and naphthyl include benzenesulfonamido, o-, m- and p- toluenesulfonamido, 3-naphthalenesulfonamido and 2-propyl-1-naphthalenesulfonamido. Examples of lower alkyl of 1 through 3 carbon atoms include methyl, ethyl, propyl and isopropyl. Examples of halogen include fluoro, chloro and bromo. Examples of lower alkoxy of 1 through 3 carbon atoms include methoxy, ethoxy, propoxy and isopropoxy. Examples of lower alkylthio of 1 through 3 carbon atoms include methylthio, ethylthio, propylthio and isopropylthio.

The novel compounds of Formulae III, IV, V, XII and XIII (i.e., VI, VII, VIII, IX, X and XI) of this invention and processes for their preparation are represented by the following sequence of formulae:

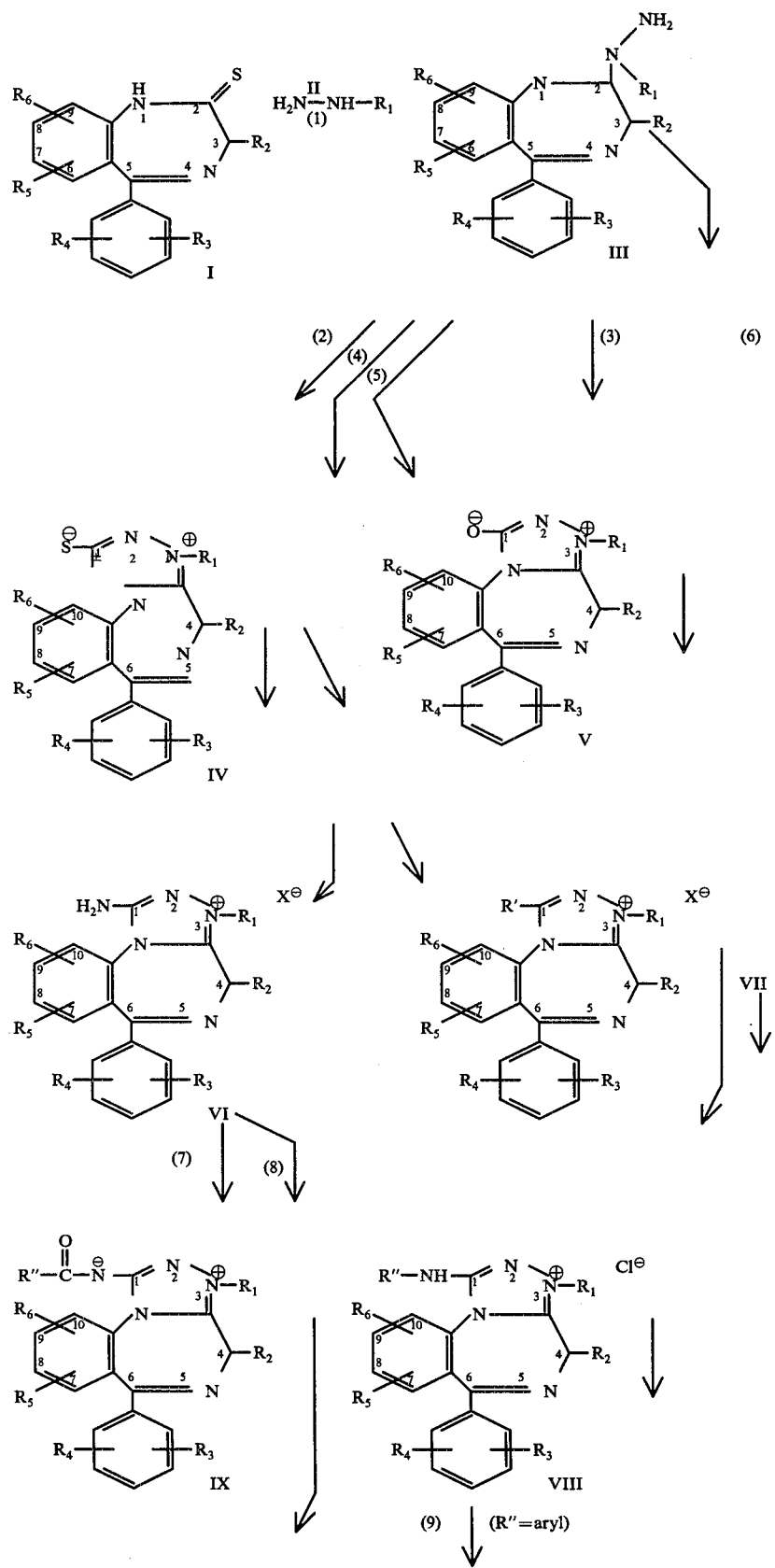

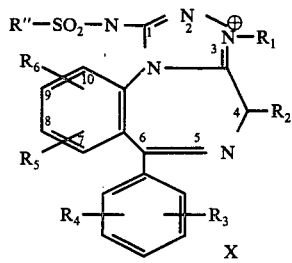
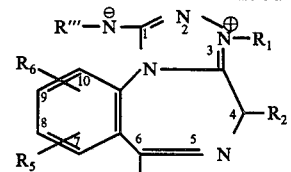
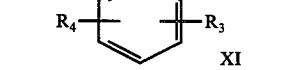
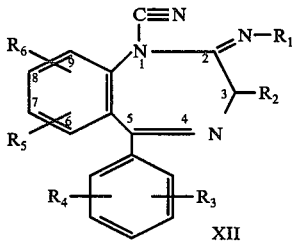

wherein R' is selected from the group consisting of hydrogen and lower alkyl of 1 through 3 carbon atoms, R" is selected from the group consisting of lower alkyl of 1 through 3 carbon atoms and aryl (i.e., unsubstituted and monosubstituted phenyl and naphthyl), R'" is aryl (i.e., unsubstituted and monosubstituted phenyl and naphthyl) and $R_1$, $R_2$, $R_3$, $R_4$, $R_5$, $R_6$, $\ominus$, and $\oplus$ have the same meaning as above.

The novel compounds embraced by Formulae II through XII of the flowsheet, above, are prepared by the procedures indicated therein, employing the method and reactions described below.

(1) The first step of the process for preparing the compounds set forth in the above flow-sheet is carried out by reacting an appropriate 1,3-dihydro-5-phenyl-2H-1,4-benzodiazepine-2-thione (I) (prepared as in U.S. Pat. No. 3,422,091) with an alkyl hydrazine (II) in a solvent such as a lower alkanol, tetrahydrofuran, dioxane and the like, at temperatures of from about 0° to about 80° C. (preferably at about 25° C.) for from about 1 to about 10 hours, to yield a corresponding 2-(1-alkylhydrazino)-5-phenyl-3H-1,4-benzodiazepine(III).

(2) The next step of the process involves slowly adding thiophosgene to a solution of a 2-(1-alkylhydrazino)-5-phenyl-3H-1,4-benzodiazepine (III) produced in step (1) and a strongly basic tertiary amine (such as triethylamine) in an inert solvent (e.g., toluene, methylene chloride, tetrahydrofuran, and the like) at low temperature (from about −20° to about 0° C.) and subsequently warming the mixture (at from about 25° to about 100° C.) to complete the reaction, to give a corresponding 1-mercapto-3-alkyl-6-phenyl-4H-s-triazolo[4,3-a][1,4]benzodiazepinium hydroxide inner salt (IV).

(3) A 2-(1-alkylhydrazino)-5-phenyl-3H-1,4-benzodiazepine (III) prepared in step (1) and a base such as triethylamine in a solvent such as tetrahydrofuran, chloroform, dioxane, methylene chloride or toluene are reacted with phosgene at from about 0° to about 25° C. (although lower or higher temperatures can be satisfactorily employed) for from about 1 to about 10 hours, to yield a corresponding anhydro-1-hydroxy-3-alkyl-6-phenyl-4H-s-triazolo[4,3-a][1,4]benzodiazepinium hydroxide (V).

(4) In this step, a 2-(1-alkylhydrazino)-5-phenyl-3H-1,4-benzodiazepine (III) produced in step (1) is reacted with cyanogen bromide in an inert solvent such as tetrahydrofuran, dioxane, benzene, toluene, methylene chloride and the like, at temperatures of from about 0° to about 80° C. for from about 1 to about 24 hours, to give a corresponding 1-amino-3-alkyl-6-phenyl-4H-s-triazolo[4,3-a][1,4]-benzodiazepinium bromide (VI), which on treatment with the chloride form of an ion exchange resin (e.g., Amberlite IRA-400) gives a corresponding chloride (VI).

(5) A 2-(1-alkylhydrazino)-5-phenyl-3H-1,4-benzodiazepine (III) prepared in step (1) is reacted with an ortho ester of an alkanoic acid (such as ethyl orthoformate, ethyl orthoacetate or methyl orthopropionate having the formula R'-C(OAlk)$_3$ wherein Alk is lower alkyl and R' is hydrogen or lower alkyl of 1 through 3 carbon atoms) and a strong acid such as sulfuric, hydrochloric, hydrobromic, methanesulfonic, toluenesulfonic and the like, in a solvent such as chloroform or methylene chloride, at temperatures of from about 0° to about 50° C., for from about 2 to about 24 hours, to give a corresponding 3-alkyl (or 1,3-dialkyl)-6-phenyl-4H-s-triazolo[4,3-a][1,4]benzodiazepinium X$^\ominus$ compound (VII) wherein X$^\ominus$ is the anion of the acid used in the reaction.

(6) A 2-(1-alkylhydrazino)-5-phenyl-3H-1,4-benzodiazepine (III) prepared in step (1) is reacted with a dichloroisocyanate [having the formula

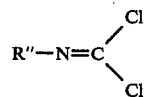

wherein R" is (a) lower alkyl of 1 through 3 carbon atoms or (b) unsubstituted and monosubstituted aryl (phenyl or naphthyl) and prepared as in Angew. Chem. Internat. Ed. 6, 649, (1967)] in an inert solvent such as methylene chloride, chloroform, benzene or toluene, at reflux temperature, for from about 1 to about 4 hours, to give a corresponding (a) 3-alkyl-1-(alkylamino)-6-phenyl-4H-s-triazolo[4,3-a][1,4]benzodiazepinium chloride (VIII) or (b) 3-alkyl-1-(arylamino)-6-phenyl-4H-s-triazolo-[4,3-a][1,4]benzodiazepinium chloride (VIII).

(7) In this step, a 1-amino-3-alkyl-6-phenyl-4H-s-triazolo[4,3-a][1,4]benzodiazepinium halide (VI) prepared in step (4) is treated at low temperature with a reactive carboxylic acid derivative (e.g., an acyl halide such as acetyl bromide, benzoyl chloride or naphthoyl chloride, an anhydride such as acetic anhydride, propionic anhydride, benzoic anhydride or naphthoic anhydride, or a mixed anhydride) in the presence of a base, e.g., a tertiary amine base such as pyridine or triethylamine in a solvent such as water, tetrahydrofuran, chloroform or an excess of a tertiary amine base such as pyridine, followed by adding to the reaction mixture an alkali metal hydroxide, carbonate or bicarbonate, to yield a corresponding 1-acyl (or aryl) amido-3-alkyl-6-phenyl-4H-s-triazolo[4,3-a][1,4]benzodiazepinium hydroxide inner salt (IX).

(8) A 1-amino-3-alkyl-6-phenyl-4H-s-triazolo[4,3-a]-[1,4]benzodiazepinium halide (VI) prepared in step (4) is treated at low temperature with an alkyl (or aryl) sulfonyl halide [having the formula R"SO$_2$X' wherein R" is (a) lower alkyl of 1 through 3 carbon atoms or (b) unsubstituted and monosubstituted aryl (phenyl or naphthyl) and X' is halogen] such as benzenesulfonyl chloride, p-toluenesulfonyl chloride, naphthalene sulfonyl bromide, methanesulfonyl bromide, methanesulfonyl chloride and the like, in the presence of a base, e.g., a tertiary amine base such as pyridine, in a solvent such as tetrahydrofuran, chloroform or an excess of pyridine, followed by adding to the reaction mixture an alkali metal hydroxide, carbonate or bicarbonate, to give a corresponding 1-alkyl (or aryl) sulfonamido-3-alkyl-6-phenyl-4H-s-triazolo[4,3-a][1,4]benzodiazepinium hydroxide inner salt (X).

(9) A 3-alkyl-1-(arylamino)-6-phenyl-4H-s-triazolo[4,3-a][1,4]benzodiazepinium chloride (VIII) prepared in step (6) is neutralized in aqueous solution with a base such as ammonium hydroxide, a tertiary amine base such as triethylamine or an alkali metal hydroxide, carbonate or bicarbonate, a temperatures of from about 0° to about 25° C., to yield a corresponding 3-alkyl-1-(arylamino)-6-phenyl-4H-s-triazolo-[4,3-a][1,4]benzodiazepinium hydroxide inner salt (XI).

(10) A 3-alkyl-6-phenyl-4H-s-triazolo[4,3-a][1,4]benzodiazepinium X$^\ominus$ compound (VII) (wherein R' is hydrogen) prepared in step (5) is reacted in aqueous solution with a strong base such as an alkali metal hydroxide (e.g., sodium or potassium hydroxide), to give a corresponding 2,3-dihydro-2-(alkylimino)-5-phenyl-1H-1,4-benzodiazepine-1-carbonitrile (XII).

All of the compounds included within Formulae III through XII of the flow-sheet, above, can be isolated from their respective reaction mixtures by conventional means, for example, when a water-miscible solvent is used, by pouring the reaction mixture into water and separating the resulting precipitate by filtration or by extraction with water-immiscible solvents. Additional purification of the products can be accomplished by conventional means, for example, by elution chromatography from an adsorbent column with a suitable solvent such as acetone, ethyl acetate, ether, chloroform, methanol, methylene chloride and Skellysolve B (hexanes), mixtures and combinations of these solvents; also by gradient elution chromatography from an adsorbent column with a suitable mixture of solvents, such as, methylene chloride-Skellysolve B, acetone-Skellysolve B, and the like.

The compounds of Formulae III through XII are useful as central nervous system (CNS) depressants when administered to humans and animals. They possess tranquilizing activity and are consequently useful in humans for controlling anxiety and schizophrenia; in animals the aforesaid compounds are useful for their calming effects and can be given to reduce anxiety and aggressive behavior. These compounds have been shown to possess CNS depressing activity via the loss of righting reflex, traction, chimney, dish and pedestal tests carried out in the manner described by Bossier et al., in Medicina Experimentalis 4, 145 (1961).

Tranquilizing effects of the compounds of this invention are shown by the following tests in mice:

Chimney test: [Med. Exp. 4, 145 (1961)]: The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. ED$_{50}$ equals the dose of test compound at which 50% of the mice remain in the dish.

Pedestal test: The untreated mouse leaves a standard pedestal in less than a minute to climb back to the floor of the standard mouse box. Tranquilized mice will stay on the pedestal for more than 1 minute.

Nicotine antagonism test: Mice in a group of 6 are injected with the test compound. Thirty minutes later the mice including control (untreated) mice are injected with nicotine salicylate (2 mg./kg.). The control mice show overstimulation, i.e., (1) running convulsions followed by (2) tonic extensor fits; followed by (3) death.

The following compounds typical of this invention have (by intraperitoneal injection in mice) ED$_{50}$ as shown in the table below.

| COMPOUND | ED$_{50}$ (mg./kg.) | | | | |
|---|---|---|---|---|---|
| | Ch | D | P | Ni(2) | Ni(3) |
| 8-chloro-6-(o-chloro-phenyl)-1-hydroxy-3-methyl-4H-s-triazolo[4,3-a][1,4]-benzodiazepinium hydroxide inner salt (V) | 1.6 | 1.2 | 3.2 | 0.3 | 0.44 |
| 8-chloro-1,3-dimethyl-6-phenyl-4H-s-triazolo[4,3-a]-[1,4]benzodiazepinium chloride (VII) | 36 | 79 | 79 | 22 | 22 |

Ch = chimney test
D = dish test
P = pedestal test
Ni = nicotine antagonism (2) and (3) tests.

As tranquilizers, the compounds of Formulae III through XII can be prepared and administered to humans, mammals, birds and animals in a wide variety of oral or parenteral dosage forms, singly or in admixture with other coacting compounds, in doses of from about 0.05 to about 1.5 mg./kg., depending on the severity of the condition being treated and the recipient's response to the medication.

The tranquilizing compounds of Formulae II through XII can be administered with a pharmaceutical carrier which can be a solid material or a liquid in which the compound is dissolved, dispersed or suspended. The solid compositions can take the form of tablets, powders, capsules, pills and the like, preferably in unit forms for simple administration or precise dosages. The liquid compositions can take the form of solutions, emulsions, suspensions, syrups, or elixirs.

DETAILED DESCRIPTION

The following examples are illustrative of the manner of making and using the invention and set forth the best mode contemplated by the inventor of carrying out his invention, but are not to be construed as limiting the scope thereof, as obvious modifications and equivalents will be apparent to those skilled in the art, and the invention is therefore to be limited only by the scope of the appended claims.

EXAMPLE 1

7-Chloro-2-(1-methylhydrazino)-5-phenyl-3H-1,4-benzodiazepine (III)

A suspension of 8.6 g. (0.03 mole) of 7-chloro-1,3-dihydro-5-phenyl-2H-1,4-benzodiazepine-2-thione (I) (prepared as in U.S. Pat. No. 3,422,091) in 600 ml. of methanol; is treated with 5.53 g. (0.12 mole) of methylhydrazine (II) and stirred at room temperature for about 2.5 hours. A vigorous stream of nitrogen is bubbled through the mixture during this period to remove liberated hydrogen sulfide. The mixture is concentrated under vacuum to a small volume, diluted with ice water and extracted with chloroform. The extract is washed with cold, dilute sodium chloride solution, dried with sodium sulfate and concentrated under vacuum. The residue is chromatographed on 400 g. of silica gel with a mixture of 1.5% methanol-98.5% chloroform. The product is crystallized on a rotary evaporator at about 25° C. by replacing the chloroform of a methanol-chloroform solution, first with ethyl acetate and then with Skellysolve B. The yields of 7-chloro-2-(1-methylhydrazino)-5-phenyl-3H-1,4-benzodiazepine (III) are 5.07 g. having a melting point of 166.6° to 173° C. and 0.52 g. having a melting point of 175° to 176° C. The analytical sample is recrystallized from ethyl acetate-Skellysolve B having a melting point of 178.5° to 179.5° C.; ultraviolet (EtOH) end absorption, λmax. 232mμ (ε=21,400), 269 (18,300), 352 (2920); infrared absorption (Nujol) 3290, 3180 cm$^{-1}$ (NH), 1645, 1590, 1575, 1565 (C=N/C=C).

Anal. Calcd. for $C_{16}H_{15}ClN_4$: C, 64.32; H, 5.06; Cl, 11.87; N, 18.75. Found: C, 63.97; H, 4.99; Cl, 12.09; N, 18.84.

Following the procedure of Example 1 but substituting another known representative 2H-1,4-benzodiazepine-2-thione (I) starting material (prepared as in U.S. Pat. No. 3,442,091) such as (1) 1,3-dihydro-5-phenyl-2H-1,4-benzodiazepine-2-thione (I),
(2) 7-chloro-1,3-dihydro-5-(2,6-dichlorophenyl)-2H-1,4-benzodiazepine-2-thione (I),
(3) 8-bromo-1,3-dihydro-5-(3,4-dimethylphenyl)-2H-1,4-benzodiazepine-2-thione (I),
(4) 7-bromo-1,3-dihydro-3-methyl-5-(2-methyl-4-methoxyphenyl)-2H-1,4-benzodiazepine-2-thione (I),
(5) 1,3-dihydro-5-(o-chlorophenyl)-2H-1,4-benzodiazepine-2-thione (I),
(6) 1,3-dihydro-7-fluoro-5-phenyl-2H-1,4-benzodiazepine-2-thione (I),
(7) 8-cyano-1,3-dihydro-5-[p-(trifluoromethyl)phenyl]-2H-1,4-benzodiazepine-2-thione (I),
(8) 7,9-dichloro-1,3-dihydro-5-(o-chlorophenyl)-2H-1,4-benzodiazepine-2-thione (I),
(9) 7-bromo-1,3-dihydro-5-phenyl-2H-1,4-benzodiazepine-2-thione (I),
(10) 5-(p-chlorophenyl)-7-chloro-1,3-dihydro-2H-1,4-benzodiazepine-2-thione (I),
(11) 6,8-diethyl-1,3-dihydro-5-(o-nitrophenyl)-9-trifluoromethyl-2H-1,4-benzodiazepine-2-thione (I),
(12) 1,3-dihydro-7-nitro-5-(o-chlorophenyl)-2H-1,4-benzodiazepine-2-thione (I),
(13) 1,3-dihydro-7-methylthio-5-phenyl-2H-1,4-benzodiazepine-2-thione (I),
(14) 7,8-dibromo-1,3-dihydro-5-(m-ethoxyphenyl)-2H-1,4-benzodiazepine-2-thione (I),
(15) 7-chloro-1,3-dihydro-8-nitro-5-[o-(trifluoromethyl)phenyl]-2H-1,4-benzodiazepine-2-thione (I),
(16) 8-bromo-1,3-dihydro-5-(2-chloro-4-fluorophenyl)-7-ethyl-2H-1,4-benzodiazepine-2-thione (I),
(17) 7,8-dibromo-1,3-dihydro-5-phenyl-3-propyl-2H-1,4-benzodiazepine-2-thione (I),
(18) 1,3-dihydro-6,7-dimethyl-3-propyl-5-(o-propylphenyl)-8-trifluoromethyl-2H-1,4-benzodiazepine-2-thione (I),
(19) 5-phenyl-7-trifluoromethyl-2H-1,4-benzodiazepine-2-thione (I),
(20) 7,8-dichloro-5-phenyl-9-trifluoromethyl-2H-1,4-benzodiazepine-2-thione (I),
(21) 6,9-dichloro-1,3-dihydro-5-(p-isopropylphenyl)-2H-1,4-benzodiazepine-2-thione,
(22) 7,8-diethyl-1,3-dihydro-5-(m-ethylphenyl)-2H-1,4-benzodiazepine-2-thione (I),
(23) 8-chloro-1,3-dihydro-6-propyl-5-(o-propylphenyl)-2H-1,4-benzodiazepine-2-thione (I),
(24) 1,3-dihydro-7-ethyl-8-fluoro-3-isopropyl-5-(o-propoxyphenyl)-2H-1,4-benzodiazepine-2-thione (I),
(25) 7-chloro-1,3-dihydro-5-(2,6-difluorophenyl)-2H-1,4-benzodiazepine-2-thione (I),
(26) 1,3-dihydro-7-nitro-5-phenyl-2H-1,4-benzodiazepine-2-thione (I),
(27) 7-cyano-1,3-dihydro-5-phenyl-2H-1,4-benzodiazepine-2-thione (I), and the like, yields, respectively, (1) 2-(1-methylhydrazino)-5-phenyl-3H-1,4-benzodiazepine (III),
(2) 7-chloro-5-(2,6-dichlorophenyl)-2-(1-methylhydrazino)-3H-1,4-benzodiazepine (III),
(3) 8-bromo-5-(3,4-dimethylphenyl)-2-(1-methylhydrazino)-3H-1,4-benzodiazepine (III),
(4) 7-bromo-3-methyl-5-(2-methyl-4-methoxyphenyl)-2-(1-methylhydrazino)-3H-1,4-benzodiazepine (III),
(5) 5-(o-chlorophenyl)-2-(1-methylhydrazino)-3H-1,4-benzodiazepine (III),
(6) 7-fluoro-2-(1-methylhydrazino)-5-phenyl-3H-1,4-benzodiazepine (III),
(7) 8-cyano-2-(1-methylhydrazino)-5-[p-(trifluoromethyl)phenyl]-3H-1,4-benzodiazepine (III),
(8) 7,9-dichloro-5-(o-chlorophenyl)-2-(1-methylhydrazino)-3H-1,4-benzodiazepine (III),
(9) 7-bromo-2-(1-methylhydrazino)-5-phenyl-3H-1,4-benzodiazepine (III),
(10) 7-chloro-5-(o-chlorophenyl)-2-(1-methylhydrazino-3H-1,4-benzodiazepine (III),
(11) 6,8-diethyl-2-(1-methylhydrazino)-5-(o-nitrophenyl)-9-trifluoromethyl-3H-1,4-benzodiazepine (III),
(12) 5-(o-chlorophenyl)-2-(1-methylhydrazino)-7-nitro-3H-1,4-benzodiazepine (III),
(13) 2-(1-methylhydrazino)-7-methylthio-5-phenyl-3H-1,4-benzodiazepine (III),

(14) 7,8-dibromo-5-(m-ethoxyphenyl)-2-(1-methylhydrazino)-3H-1,4-benzodiazepine (III),
(15) 7-chloro-2-(1-methylhydrazino)-8-nitro-5-[o-(trifluoromethyl)phenyl]-3H-1,4-benzodiazepine (III),
(16) 8-bromo-5-(2-chloro-4-fluorophenyl)-7-ethyl-2-(1-methylhydrazino)-3H-1,4-benzodiazepine (III),
(17) 7,8-dibromo-2-(1-methylhydrazino)-5-phenyl-3H-1,4-benzodiazepine (III),
(18) 6,7-dimethyl-2-(1-methylhydrazino)-3-propyl-5-(o-propylphenyl)-8-trifluoromethyl-3H-1,4-benzoidazepine (III),
(19) 5-phenyl-2-(1-methylhydrazino)-7-trifluoromethyl-3H-1,4-benzodiazepine (III),
(20) 7,8-dichloro-2-(1-methylhydrazino)-5-phenyl-9-trifluoromethyl-3H-1,4-benzodiazepine (III),
(21) 6,9-dichloro-5-(p-isopropylphenyl)-2-(1-methylhydrazino)-3H-1,4-benzodiazepine (III),
(22) 7,8-diethyl-5-(m-ethylphenyl)-2-(1-methylhydrazino)-3H-1,4-benzodiazepine (III),
(23) 8-chloro-2-(1-methylhydrazino)-6-propyl-5-(o-propylphenyl)-3H-1,4-benzodiazepine (III),
(24) 7-ethyl-8-fluoro-3-isopropyl-2-(1-methylhydrazino)-5-(o-propoxyphenyl)-3H-1,4-benzodiazepine (III),
(25) 7-chloro-5-(2,6-difluorophenyl)-2-(1-methylhydrazino)-3H-1,4-benzodiazepine (III),
(26) 2-(1-methylhydrazino)-7-nitro-5-phenyl-3H-1,4-benzodiazepine (III),
(27) 7-cyano-2-(1-methylhydrazino)-5-phenyl-3H-1,4-benzodiazepine (III), and the like, Following the procedure of Example 1 but substituting another known representative 2H-1,4-benzodiazepine-2-thione (I) and reacting it with another known lower alkyl hydrazine, such as
(1) 5-(o-bromophenyl)-7-chloro-1,3-dihydro-2H-1,4-benzodiazepine-2-thione (I) and ethyl hydrazine,
(2) 7-bromo-1,3-bromo-1,3-dihydro-5-(o-nitrophenyl)-2H-1,4-benzodiazepine-2-thione (I) and propyl hydrazine,
(3) 1,3-dihydro-7-fluoro-5-[o-(trifluoromethyl)phenyl]-2H-1,4-benzodiazepine-2-thione (I) and isopropyl hydrazine, and the like,
yields, respectively,
(1) 5-(o-bromophenyl)-7-chloro-2-(1-ethylhydrazino)-3H-1,4-benzodiazepine (III),
(2) 7-bromo-2-(1-propylhydrazino)-5-(o-nitrophenyl)-3H-1,4-benzodiazepine (III),
(3) 7-fluoro-2-(1-isopropylhydrazino)-5-[o-(trifluoromethyl)phenyl]-3H-1,4-benzodiazepine (III), and the like.

EXAMPLE 2

8-Chloro-1-mercapto-3-methyl-6-phenyl-4H-s-triazolo[4,3-a][1,4]benzodiazepinium hydroxide inner salt (IV)

A stirred mixture of 4.48 g. (0.015 mole) of 7-chloro-2-(1-methylhydrazino)-5-phenyl-3H-1,4-benzodiazepine (III), (prepared as in Example 1), 4.68 ml. (0.033 mole) of triethylamine and 60 ml. of tetrahydrofuran is cooled, under nitrogen, in a salt bath, and treated dropwise during about 1 hour and 20 minutes with a solution of 1.26 ml. of thiophosgene in 30 ml. of tetrahydrofuran. The mixture is allowed to warm slowly to room temperature, stand for about 16 hours and heated under reflux for about 70 minutes. The mixture, after cooling, is poured into ice water, the solid collected by filtration, dissolved in chloroform, washed with brine and dried with sodium sulfate. The aqueous filtrate is concentrated under vacuum to remove tetrahydrofuran and then extracted with chloroform. The extract is washed with brine and dried with sodium sulfate. The chloroform solutions are combined and concentrated and the residue chromatographed on 300 g. of silica gel with 2% methanol-98% chloroform. The product thus obtained is recrystallized from a mixture of methylene chloride and methanol to give a first crop weighing 1.33 g. with a melting point of 261.5° to 267° C. (with decomposition) and a second weighing 1.94 g. with a melting point of 258° to about 267° C. (with decomposition) with softening at 245° C. These two samples are apparently different polymorphic crystalline forms since they have different solubility in methylene chloride-methanol, different infrared (ir) (Nujol) absorption spectra but identical ultraviolet (uv) (EtOH) absorption spectra and nuclear magnetic resonance (nmr) (DMSO) spectra. They also show the same empirical formulae by elemental and mass spectral analysis. The second crop is recrystallized twice from methylene chloride-methanol for analysis. The analytical sample of this crop of the product, 8-chloro-1-mercapto-3-methyl-6-phenyl-4H-s-triazolo[4,3-a][1,4]benzodiazepinium hydroxide inner salt (IV), has a melting point of 258° to 262° C. (with decomposition) with softening at 245° C.; uv (EtOH) λmax. 219.5 mμ (ε=46,100), 245 (shoulder 19,150), 260 (sh 11,250), 278 (sh 8250), 310 (sh 4200). The ir, nmr and mass spectra of the compound support its proposed structure.

Anal. Calcd. for $C_{17}H_{13}ClN_4S$: C, 59.91; H, 3.84; Cl, 10.40; N, 16.44; S, 9.41. Found: C, 59.99; H, 3.99; Cl, 10.64; N, 16.81; S, 9.38.

Following the procedure of Example 2 but substituting other compounds of Formula III as starting materials, such as
(1) 7-bromo-2-(1-methylhydrazino)-5-(o-fluorophenyl)-3H-1,4-benzodiazepine (III),
(2) 7-chloro-2-(1-ethylhydrazino)-5-(o-chlorophenyl)-3H-1,4-benzodiazepine (III),
(3) 2-(1-methylhydrazino)-5-(o-chlorophenyl)-3H-1,4-benzodiazepine (III),
(4) 6,9-dimethoxy-5-(2-fluoro-4-cyanophenyl)-2-(1-propylhydrazino)-3H-1,4-benzodiazepine (III),
(5) 7-chloro-9-ethyl-3-methyl-2-(1-methylhydrazino)-5-(2-nitro-5-trifluoromethylphenyl)-3H-1,4-benzodiazepine (III), and the like, yields, respectively,
(1) 8-bromo-3-methyl-6-(o-fluorophenyl)-1-mercapto-4H-s-triazolo[4,3-a][1,4]benzodiazepinium hydroxide inner salt (IV),
(2) 3-ethyl-6-(o-chlorophenyl)-8-chloro-1-mercapto-4H-s-triazolo[4,3-a][1,4]benzodiazepinium hydroxide inner salt (IV),
(3) 3-methyl-1-mercapto-6-(o-chlorphenyl)-4H-s-triazolo[4,3-a][1,4]benzodiazepinium hydroxide inner salt (IV),
(4) 7,10-dimethoxy-6-(2-fluoro-4-cyanophenyl)-1-mercapto-3-propyl-4H-s-triazolo[4,3-a][1,4]benzodiazepinium hydroxide inner salt (IV),
(5) 8-chloro-3,4-dimethyl-10-ethyl-1-mercapto-6-(2-nitro-5-trifluoromethylphenyl)-4H-s-triazolo[4,3-a][1,4]-benzodiazepinium hydroxide inner salt (IV), and the like.

EXAMPLE 3

Anhydro-8-chloro-1-hydroxy-3-methyl-6-phenyl-4H-s-triazolo[4,3-a][1,4]benzodiazepinium hydroxide (V)

Into a stirred ice-cold mixture of 1.5 g. (0.005 mole) of 7-chloro-2-(1-methylhydrazino)-5-phenyl-3H-1,4-benzodiazepine (III), 15 ml. of tetrahydrofuran and 1.53 g. (0.011 mole) of triethylamino, 0.4 ml. (0.0055 mole) of phosgene is evaporated during a period of about 45 minutes. The mixture becomes very thick and after about 1 hour an additional 10 ml. of tetrahydrofuran is added. The mixture is allowed to warm to room temperature and stand for about 6 hours, after which time it is poured into ice water. The mixture is neutralized with sodium bicarbonate and extracted with chloroform. The extract is washed with brine, dried with sodium sulfate and concentrated under vacuum. The residue is crystallized from a mixture of methanol and ethyl acetate to give 1.1 g. of product having a melting point of 285° to 286° C and 0.184 g. melting at 275° to 276° C. The analytical sample of the product, anhydro-8-chloro-1-hydroxy-3-methyl-6-phenyl-4H-s-triazolo[4,3-a][1,4]benzodiazepinium hydroxide (V), has a melting point of 289.5° to 290° C. (with decomposition); uv (EtOH) λmax. 220 mμ (ε=34,050), 266 (15,200); ir (Nujol) 1690, shoulder 1660, 1620, 1610, 1590, 1575, 1565, 1510 (C=O/C=N/C=C). The nmr and mass spectra of the compound support its proposed structure.

Anal. Calcd. for $C_{17}H_{13}ClN_4O$: C, 62.87; H, 4.03; Cl, 10.92 N, 17.25. Found: C, 62.23; H, 4.06; Cl, 10.93; N, 17.17.

Following the procedure of Example 3 but substituting other compounds of Formula III as starting materials, such as (1) 7-chloro-2-(1-ethylhydrazino)-5-(2-ethoxy-5-methoxyphenyl)-8-ethyl-3H-1,4-benzodiazepine (III), (2) 8-bromo-2-(1-ethylhydrazino)-5-(3-methylthio-6-nitrophenyl)-9-propyl-3H-1,4-benzodiazepine (III), (3) 8-cyano-2-(1-ethylhydrazino)-7-fluoro-5-(2-methyl-4-propylthiophenyl)-3H-1,4-benzodiazepine (III), (4) 6-chloro-8-ethoxy-5-(3-ethyl-5-fluorophenyl)-2-(1-propylhydrazino)-3H-1,4-benzodiazepine (III), (5) 7-bromo-2-(1-methylhydrazino)-5-(2,6-difluorophenyl)-3H-1,4-benzodiazepine (III), and the like, yields, respectively, (1) anhydro-8-chloro-6-(2-ethoxy-5-methoxyphenyl)-3,9-diethyl-1-hydroxy-4H-s-triazolo[4,3-a][1,4]benzodiazepinium hydroxide (V), (2) anhydro-9-bromo-3-ethyl-1-hydroxy-6-(3-methylthio-6-nitrophenyl)-10-propyl-4H-s-triazolo[4,3-a][1,4]benzodiazepinium hydroxide (V), (3) anhydro-9-cyano-3-ethyl-8-fluoro-1-hydroxy-6-(2-methyl-4-propylthiophenyl)-4H-s-triazolo[4,3-a][1,4]benzodiazepinium hydroxide (V), (4) anhydro-7-chloro-9-ethoxy-6-(3-ethyl-5-fluorophenyl)-1-hydroxy-3-propyl-4H-s-triazolo[4,3-a][1,4]benzodiazepinium hydroxide (V), (5) anhydro-8-bromo-6-(2,6-difluorophenyl)-1-hydroxy-3-methyl-4H-s-triazolo[4,3-a][1,4]benzodiazepinium hydroxide (V), and the like.

EXAMPLE 4

8-Chloro-6-(o-chlorophenyl)-1-hydroxy-3-methyl-4H-s-triazolo[4,3-a][1,4]benzodiazepinium hydroxide inner salt (V)

A. A stirred mixture of 6.42 g. (0.02 mole) of 7-chloro-5-(o-chlorophenyl)-1,3-dihydro-2H-1,4-benzodiazepine-2-thione (I) (prepared as in J. Org. Chem. 29, 231) and 400 ml. of methanol is treated with 3.68 g. (0.08 mole) of methyl hydrazine (II) and kept at room temperature for about 16 hours with a stream of nitrogen bubbling through the mixture. The methanol is then concentrated under vacuum at a bath temperature of about 30° C., ethyl acetate being added to the mixture slowly as the methanol is evaporated. This permits the product to crystallize to give 4.03 g. with a melting point of 160° to 163° C., 0.76 g. melting at 160° to 163° C. and 0.56 g. with a melting point of 158° to 161° C. of 7-chloro-5-(o-chlorophenyl)-2-(1-methylhydrazino)-3H-1,4-benzodiazepine (III).

B. A stirred solution of 3.33 g. (0.01 mole) of 7-chloro-5-(o-chlorophenyl)-2-(1-methylhydrazino)-3H-1,4-benzodiazepine (III) (obtained in A, above) and 3.06 ml. (0.022 mole) of triethylamine in 50 ml. of tetrahydrofuran, under nitrogen, is cooled in an ice bath and treated with 0.8 ml. (0.011 mole) of phosgene by slowly evaporating the liquid into the reaction mixture during the course of about 45 minutes. The thick mixture is kept for an additional 1 hour in an ice bath and about 5.5 hours at room temperature. It is then poured into ice water, neutralized with sodium bicarbonate and extracted with chloroform. The extract is washed with brine, dried with sodium sulfate and concentrated. The residue is crystallized from a mixture of methanol and ethyl acetate to give 0.76 g. melting at 239.5° to 242° C., 1.25 g. melting at 238.5° to 241° C. and 0.75 g. melting at 237° to 239° C. of 8-chloro-6-(o-chlorophenyl)-1-hydroxy-3-methyl-4H-s-triazolo[4,3-a][1,4]-benzodiazepinium hydroxide inner salt (V). The analytical sample shows: melting point 239.5° to 242° C.; uv (EtOH) end absorption λmax. 218 mμ (ε=36,200), 268 (ε=11,950). The ir and nmr spectra support the structure proposed for the compound.

Anal. Calcd. for $C_{17}H_{12}Cl_2N_4O$: C, 56.84; H, 3.37; Cl, 19.74; N, 15.60. Found: C, 56.90; H, 3.41; Cl, 19.80; N, 15.66.

EXAMPLE 5

1-Amino-8-chloro-3-methyl-6-phenyl-4H-s-triazolo[4,3-a][1,4]benzodiazepinium chloride (VI)

A. A stirred mixture of 8.97 g. (0.03 mole) of 7-chloro-2-(1-methylhydrazino)-5-phenyl-3H-1,4-benzodiazepine (III) and 75 ml. of dioxane is cooled, under nitrogen, in an ice bath and treated during about 20 minutes with a solution of 3.18 g. of cyanogen bromide in 30 ml. of dioxane. The mixture is kept at room temperature for about 17 hours and at about 69° to about 79° C. for about 3 hours, then cooled and filtered. The collected solid is washed with dioxane, dissolved in 500 ml. of warm, absolute ethanol, the resulting solution decolorized with activated carbon (Darco G60) and crystallized by slowly concentrating it under vacuum at about 25° C. This gives 5.11 g. of product (VI) melting at 263° to 265° C. (with decomposition) and 1.11 g. melting at 258° to 261° C. (with decomposition). This material is difficult to work with and attempts to purify it by recrystallization from methanol-ethyl acetate or ethanol resulting in its almost complete decomposition. An analytical sample is obtained by recrystallizing some of this material several times under mild conditions from methylene chloride-ethanol and once from ethanol to give 1-amino-8-chloro-3-methyl-6-phenyl-4H-s-triazolo[4,3-a][1,4]benzodiazepinium bromide (VI), with a melting point of 262°–263° C. (with decomposition); uv (EtOH) end absorption, λmax. 218 mμ (ε=32,300), 257 (14,250). Their ir and nmr spectra support the structure proposed for the compound.

Anal. Calcd. for $C_{17}H_{15}BrClN_5$: C, 50.45; H, 3.74; Br, 19.75; Cl, 8.76; N, 17.30. Found C, 50.35; H, 3.67; Br, 19.53; Cl, 8.61; N, 18.08.

B. A mixture of 1 g. of 1-amino-8-chloro-2-methyl-6-phenyl-4H-s-triazolo[4,3-a][1,4]benzodiazepinium bromide (VI) (prepared in A, above) and 40 ml. of water is passed through a column of the chloride form of Amberlite ® IRA-400 (Rohm and Haas Co.) ion exchange resin. The column is eluted with water, the eluate concentrated under acuum and the residue dissolved in absolute ethanol and concentrated. The resulting material is crystallized from ethanol to give 0.207 g. with a melting point of 264.5° to 266.5° C. (with decomposition) and 0.32 g. with a melting point of 260.5° to 262° C. (with decomposition) of the product, 1-amino-8-chloro-3-methyl-6-phenyl-4H-s-triazolo[4,3-a][1,4]benzodiazepinium chloride (VI). The analytical sample is prepared by crystallizing some of this material twice from ethanol. It has a melting point of 269° C. (with decomposition), uv (EtOH) λmax. 217 mμ (ε=33,000), 257 (14,200). The ir, nmr and mass spectra support the proposed for the compound.

Anal. Calcd. for $C_{17}H_{15}Cl_2N_5$: C, 56.68; H, 4.20; Cl, 19.68; N, 19.44. Found: C, 56.20; H, 4.37; Cl, 19.68; N, 19.17.

Following the procedure of Example 5 but substituting other compounds of Formula III as starting materials in A, such as
   (1) 6-bromo-2-(1-ethylhydrazino)-5-(3-fluoro-6-methylphenyl)-8-propyl-3H-1,4-benzodiazepine (III),
   (2) 7-chloro-2-(1-ethylhydrazino)-5-(2-methylthiophenyl)-8-nitro-3H-1,4-benzodiazepine (III),
   (3) 8-bromo-6-cyano-2-(1-isopropylhydrazino)-5-(2-methoxy-6-nitrophenyl)-3H-1,4-benzodiazepine (III),
   (4) 6-fluoro-8-methoxy-2-(1-methylhydrazino)-5-(3-nitro-5-propylphenyl)-7-propylthio-3H-1,4-benzodiazepine (III),
   (5) 9-bromo-7-ethyl-3-methyl-2-(1-propylhydrazino)-5-(p-trifluoromethylphenyl)-3H-1,4-benzodiazepine (III),
   (6) 2-(1-methylhydrazino)-7-nitro-5-phenyl-3H-1,4-benzodiazepine (III),
   (7) 7-chloro-5-(o-chlorophenyl)-2-(1-methylhydrazino)-3H-1,4-benzodiazepine (III), and the like,
yields, respectively,
   (1) 1-amino-7-bromo-3-ethyl-6-(3-fluoro-6-methylphenyl)-9-propyl-4H-s-triazolo[4,3-a][1,4]benzodiazepinium chloride (VI),
   (2) 1-amino-8-chloro-3-ethyl-6-(2-methyl-5-methylthiophenyl)-9-nitro-4H-s-triazolo[4,3-a][1,4]benzodiazepinium chloride (VI),
   (3) 1-amino-9-bromo-7-cyano-3-isopropyl-6-(2-methoxy-6-nitrophenyl)-4H-s-triazolo[4,3-a][1,4]benzodiazepinium chloride (VI),
   (4) 1-amino-7-fluoro-9-methoxy-3-methyl-6-(3-nitro-5-propylphenyl)-8-propylthio-4H-s-tirazolo[4,3-a][1,4]benzodiazepinium chloride (VI),
   (5) 1-amino-10-bromo-8-ethyl-4-methyl-3-propyl-6-(p-trifluoromethylphenyl)-4H-s-triazolo[4,3-a][1,4]benzodiazepinium chloride (VI),
   (6) 1-amino-3-methyl-6-phenyl-8-nitro-4H-s-triazolo[4,3-a][1,4]benzodiazepinium chloride (VI),
   (7) 1-amino-8-chloro-6-(o-chlorophenyl)-3-methyl-4H-s-triazolo[4,3-a][1,4]benzodiazepinium chloride (VI), and the like.

EXAMPLE 6

8-Chloro-3-methyl-6-phenyl-4H-s-triazolo[4,3-a][1,4]benzodiazepinium chloride (VII)

A stirred solution of 2.4 g. of 7-chloro-2-(1-methylhydrazino)-5-phenyl-3H-1,4-benzodiazepine (III) and 6.4 ml. of triethyl orthoformate in 64 ml. of chloroform is treated with 1.6 g. of sulfuric acid and kept at room temperature, under nitrogen, for about 18 hours. The solid is collected by filtration, washed with chloroform and dried to give 3.87 g. of crude 8-chloro-3-methyl-6-phenyl-4H-s-triazolo[4,3-a][1,4]benzodiazepinium hydrogen sulfate. A solution of this material in water is poured onto a column of the chloride form of Amberlite ® IRA-400 ion exchange resin. The column is eluted with water and the eluate concentrated under vacuum. A solution of the residue is dissolved in absolute ethanol and concentrated under vacuum. This material is a mixture of the desired benzodiazepinium chloride and its hydrochloride salt. It is therefore dissolved in a small volume of saturated aqueous sodium chloride, neutralized with sodium bicarbonate and extracted four times with chloroform. The extract is washed with brine, dried with sodium sulfate and concentrated under vacuum. The residue is crystallized from ethanol-ethyl acetate to give 1.05 g. melting at 213° to 214° C. (with decomposition) and 0.864 g. melting at 207° to 209° C. (with decomposition) of 8-chloro-3-methyl-6-phenyl-4H-s-triazolo[4,3-a][1,4]benzodiazepinium chloride (VII). The analytical sample melts at 214° to 217° C. (with decomposition), uv (EtOH) end absorption, λmax. 224 mμ (ε=35,050), 250 (shoulder 12,200), 265 (sh 6950), 285 (sh 4050). The ir, nmr and mass spectra support the structure proposed for the compound.

Anal. Calcd. for $C_{17}H_{14}Cl_2N_4$: C, 58.97; H, 4.37; Cl, 20.48; N, 16.18; Found: C, 58.20; H, 4.55. Cl, 18.52; N, 14.67; $H_2O$, 0.92; EtOAc, 9.72.

The analytical data recalculated on the basis of the observed $H_2O$ and EtOAc gives: C, 59.19; H, 4.01; Cl, 20.85; N, 16.33.

Heating the hydrated, solvated compound at about 100° C. in a vacuum for about 24 hours yields the corresponding anhydrous compound having the empirical formula $C_{17}H_{14}Cl_2N_4$.

Following the procedure of Example 6 but substituting other compounds of Formula III as starting materials, such as
   (1) 6-chloro-2-(1-ethylhydrazino)-5-(2-fluoro-4-methylphenyl)-7-propyl-3H-1,4-benzodiazepine (III),
   (2) 7-bromo-3-ethyl-8-nitro-5-(3-propoxy-5-trifluoromethylphenyl)-2-(1-propylhydrazino)-3H-1,4-benzodiazepine (III),
   (3) 6-fluoro-7-isopropylthio-2-(1-methylhydrazino)-5-(3-nitro-6-propylphenyl)-3H-1,4-benzodiazepine (III), and the like, yields, respectively,
(1) 7-chloro-3-ethyl-6-(2-fluoro-4-methylphenyl)-8-propyl-4H-s-triazolo[4,3-a][1,4]benzodiazepinium chloride (VII),
(2) 8-bromo-4-ethyl-9-nitro-6-(3-propoxy-5-trifluoromethyl)-3-propyl-4H-s-triazolo[4,3-a][1,4]benzodiazepinium chloride (VII),
(3) 7-fluoro-8-isopropylthio-3-methyl-6-(3-nitro-6-propylphenyl)-4H-s-triazolo[4,3-a][1,4]benzodiazepinium chloride (VII), and the like.

EXAMPLE 7

8-Chloro-1,3-dimethyl-6-phenyl-4H-s-triazolo[4,3-a][1,4]benzodiazepinium p-toluenesulfonate (VII)

A stirred mixture of 5.58 g. (0.02 mole) of 7-chloro-2-(1-methylhydrazino)-5-phenyl-3H-1,4-benzodiazepine (III), 22.6 ml. of triethyl orthoacetate and 100 ml. of chloroform, under nitrogen, is treated with 4.19 g. (0.022 mole) of p-toluenesulfonic acid hydrate and kept at room temperature about 4 hours and at reflux for about a half hour. The cooled reaction mixture is concentrated under vacuum and the residue mixed with ether and allowed to crystallize. The solid is collected by filtration, washed with ether and recrystallized from ethanol-ethyl acetate (Darco), to give 7.51 g. with a melting point of 118° C. (with decomposition), 0.821 g. with a melting point of 108° (with decomposition) and 0.653 g. with a melting point of 102° C. (with decomposition) of 8-chloro-1,3-dimethyl-6-phenyl-4H-s-triazolo[4,3-a][1,4]benzodiazepinium p-toluenesulfonate (VII). The analytical sample has a melting point of 149° to 152° C. (with decomposition) with softening at 113° C., uv (EtOH) end absorption, λmax. 223 mμ ($\epsilon$=50,400), 250 (shoulder 13,200), 262 (sh 8600), 266 (sh 8030), 271 (sh 7280), 277 (sh 6020), 285 (sh 5020), 295 (sh 3180). The ir, nmr and mass spectra support the structure proposed for the compound.

Anal. Calcd. for $C_{25}H_{23}ClN_4O_3S \cdot C_4H_8O_2$: C, 59.73; H, 5.34; Cl, 6.08; N, 9.61; S, 5.50; EtOAc, 15.11. Found: C, 59.80; H, 5.37; Cl, 6.20; N, 9.85; S, 5.75; EtOAc, 13.8.

Heating the solvated compound at about 100° C. in a vacuum oven yields the corresponding anhydrous compound having the empirical formula $C_{25}H_{23}ClN_4O_3S$.

Following the procedure of Example 7 but substituting other compounds of Formula III as starting materials, such as
(1) 7-bromo-8-ethylthio-2-(1-methylhydrazino)-5-(2-nitro-5-trifluoromethylphenyl)-3-propyl-3H-1,4-benzodiazepine (III),
(2) 7-chloro-8-cyano-2-(1-ethylhydrazino)-5-(3-propyl-6-propylthiophenyl)-3H-1,4-benzodiazepine (III), and the like,
yields, respectively,
(1) 8-bromo-1,3-dimethyl-9-ethylthio-6-(2-nitro-5-trifluoromethylphenyl)-4-propyl-4H-s-triazolo[4,3-a][1,4]benzodiazepinium p-toluenesulfonate (VII),
(2) 8-chloro-9-cyano-3-ethyl-1-methyl-6-(3-propyl-6-propylthiophenyl)-4H-s-triazolo[4,3-a][1,4]benzodiazepinium p-toluenesulfonate (VII).

Following the procedure of Example 7, but substituting ethyl orthopropionate for ethyl orthoacetate, yields 8-chloro-1-ethyl-3-methyl-6-phenyl-4H-s-triazolo[4,3-a][1,4]benzodiazepinium p-toluenesulfonate (VII).

EXAMPLE 8

8-Chloro-1,3-dimethyl-6-phenyl-4H-s-triazolo[4,3-a][1,4]benzodiazepinium chloride sesquihydrate (VII)

A solution of 1.5 g. of 8-chloro-1,3-dimethyl-6-phenyl-4H-s-triazolo[4,3-a][1,4]benzodiazepinium p-toluenesulfonate (VII) (prepared as in Example 7) in 25 ml. of water is poured through a column containing 20 g. of the chloride form of Amberlite® IRA-400 ion exchange resin. The column is eluted with water, the resulting solution concentrated under vacuum and the residue redissolved in absolute ethanol and concentrated. The resulting material is crystallized from methanol-ethyl acetate to give 1.06 g. of 8-chloro-1,3-dimethyl-6-phenyl-4H-s-triazolo[4,3-a][1,4]benzodiazepinium chloride sesquihydrate (VII). The analytical has a melting point of 170.5° C.; (EtOH) λmax. 223 mμ ($\epsilon$=38,000), 247 (sh 13,720), 265 (sh 766-), 285 (sh 4870). The ir and nmr support the structure proposed for the compound.

Anal. Calcd. for $C_{18}H_{16}Cl_2N_4 \cdot 1\ 1/2H_2O$: C, 55.97; H, 4.96; Cl, 18.36; N, 14.50; $H_2O$, 6.99. Found: C, 56.02; H, 4.55; Cl, 18.85; N, 14.32; $H_2O$, 7.38.

Heating the hydrated compound at about 100° C. in a vacuum oven for about 24 hours yields the corresponding anhydrous compound having the empirical formula $C_{18}H_{16}Cl_2N_4$.

Following the procedure of Example 8 but substituting other p-toluenesulfonate compounds of Formula VII as starting materials, such as
(1) 7-bromo-1,3-dimethyl-8-ethyl-6-(2-fluoro-6-methylphenyl)-4H-s-triazolo[4,3-a][1,4]benzodiazepinium p-toluenesulfonate (VII),
(2) 6-chloro-7-cyano-3-ethyl-1,4-dimethyl-6-(3-methylthio-5-nitrophenyl)-4H-s-triazolo[4,3-a][1,4]benzodiazepinium p-toluenesulfonate (VII),
(3) 7-fluoro-8-nitro-6-(2-propyl-5-trifluoromethylphenyl)-1,3,4-trimethyl-4H-s-triazolo[4,3-a][1,4]benzodiazepinium p-toluenesulfonate (VII), and the like,
yields, respectively,
(1) 7-bromo-1,3-dimethyl-8-ethyl-6-(2-fluoro-6-methylphenyl)-4H-s-triazolo[4,3-a][1,4]benzodiazepinium chloride (VII),
(2) 6-chloro-7-cyano-3-ethyl-1,4-dimethyl-6-(3-methylthio-5-nitrophenyl)-4H-s-triazolo[4,3-a][1,4]benzodiazepinium chloride (VII),
(3) 7-fluoro-8-nitro-6-(2-propyl-5-trifluoromethylphenyl)-1,3,4-trimethyl-4H-s-triazolo[4,3-a][1,4]benzodiazepinium chloride (VII), and the like.

EXAMPLE 9

8-Chloro-3-methyl-1-(methylamino)-6-phenyl-4H-s-triazolo[4,3-a][1,4]benzodiazepinium chloride (VIII)

A stirred mixture of 2.99 g. (0.01 mole) of 7-chloro-2-(1-methylhydrazino)-5-phenyl-3H-1,4-benzodiazepine (III) and 40 ml. of toluene is cooled in an ice bath and treated with a solution of 1.23 g. (0.011 mole) of methylisocyanide dichloride (prepared as in Angew. Chem. Internat. Ed. 6, 649) in 15 ml. of tetrahydrofuran. The mixture is kept at room temperature for about 6 hours and at reflux for about 2 hours. It is then concentrated under vacuum and the residue crystallized to give 8-chloro-3-methyl-1-(methylamino)-6-phenyl-4H-s-triazolo[4,3-a][1,4]benzodiazepinium chloride (VIII).

Following the procedure of Example 9 but substituting other compounds of Formula III as starting materials, such as (1) 2-(1-methylhydrazino)-5-phenyl-3H-1,4-benzodiazepine (III),
(2) 7-bromo-3-methyl-5-(2-methyl-5-propoxyphenyl)-2-(1-methylhydrazino)-3H-1,4-benzodiazepine (III),
(3) 5-(o-bromophenyl)-7-chloro-2-(1-ethylhydrazino)-3H-1,4-benzodiazepine (III),
(4) 7-chloro-8-ethyl-3-methyl-2-(1-propylhydrazino)-6-(p-nitrophenyl)-3H-1,4-benzodiazepine (III),
(5) 7-trifluoromethyl-2-(1-isopropylhydrazino)-3-methyl-5-(o-fluorophenyl)-3H-1,4-benzodiazepine (III), and the like, yields, respectively, (1) 3-methyl-1-(methylamino)-6-phenyl-4H-s-triazolo[4,3-a][1,4]benzodiazepinium chloride (VIII),
(2) 8-bromo-3,4-dimethyl-6-(2-methyl-5-propoxyphenyl)-1-(methylamino)-4H-s-triazolo[4,3-a][1,4]benzodiazepinium chloride (VIII),
(3) 6-(o-bromophenyl)-8-chloro-3-ethyl-1-(methylamino)-4H-s-triazolo[4,3-a][1,4]benzodiazepinium chloride (VIII),
(4) 8-chloro-9-ethyl-4-methyl-6-(p-nitrophenyl)-3-propyl-1-(methylamino)-4H-s-triazolo[4,3-a][1,4]benzodiazepinium chloride (VIII),
(5) 8-trifluoromethyl-3-isopropyl-4-methyl-1-(methylamino)-6-(o-fluorophenyl)-4H-s-triazolo[4,3-a][1,4]benzodiazepinium chloride (VIII), and the like.

Following the procedure of Example 9 but substituting ethylisocyanide dichloride or propylisocyanide dichloride, yields 8-chloro-3-methyl-1-[(ethylamino) or (propylamino)]-6-phenyl-4H-s-triazolo[4,3-a][1,4]benzodiazepinium chloride (VIII).

EXAMPLE 10

1-Acetamido-8-chloro-3-methyl-6-phenyl-4H-s-triazolo[4,3-a][1,4]benzodiazepinium hydroxide inner salt (IX)

To an ice cold stirred mixture of 8 ml. of triethylamine and 4 ml. of acetic anhydride, 1.427 g. (0.00396 mole) of 1-amino-8-chloro-3-methyl-6-phenyl-4H-s-triazolo[4,3-a][1,4]benzodiazepinium chloride (VI) (prepared as in Example 5) is added under nitrogen. The resulting mixture is kept in an ice bath for about 7 hours, treated with 10 ml. of absolute ethanol and allowed to warm slowly to room temperature during the course of about 15 hours. The mixture is concentrated under vacuum and the residue mixed with dilute aqueous sodium bicarbonate solution and extracted with chloroform. The extract is washed with brine, dried with potassium carbonate and concentrated under vacuum. The residue is dissolved in methanol, decolorized with activated carbon (Darco) and crystallized from a mixture of methanol and ethyl acetate (wet) to give 0.317 g. melting at 170° to 171° C. (with decomposition) and 0.264 g. melting at 170° to 171° C. (with decomposition) of 1-acetamido-8-chloro-3-methyl-6-phenyl-4H-s-triazolo[4,3-a][1,4]benzodiazepinium hydroxide inner salt, hydrate (IX). The analytical sample has a melting point of 169°–171° C. (with decomposition).

Anal. Calcd. for $C_{19}H_{16}ClN_5O$: C, 62.38; H, 4.41; Cl, 9.69; N, 19.14. Found: C, 60.18; H, 4.76; Cl, 9.48; N, 18.44; L $H_2O$, 4.04.

Recalculation of the analytical data based on the observed water gives: C, 62.71; H, 4.50; Cl, 9.88; N, 19.22.

Following the procedure of Example 10 but substituting other compounds of Formula VI and other anhydrides, such as (1) 1-amino-3-ethyl-6-(o-fluorophenyl)-8-nitro-4H-s-triazolo[4,3-a][1,4]benzodiazepinium chloride (VI) and propionic anhydride,
(2) 1-amino-8-methylthio-3-methyl-4H-s-triazolo[4,3-a][1,4]benzodiazepinium chloride (VI) and butyric anhydride,
(3) 1-amino-8-cyano-3-ethyl-6-(o-chlorophenyl)-4H-s-triazolo[4,3-a][1,4]benzodiazepinium chloride (VI) and benzoic anhydride, and the like, yields, respectively, (1) 3-ethyl-6-(o-fluorophenyl)-8-nitro-1-propionamido-4H-s-triazolo[4,3-a][1,4]benzodiazepinium hydroxide inner salt (IX),
(2) 1-butyramidophenyl-3-methyl-8-methylthio-4H-s-triazolo[4,3-a][1,4]benzodiazepinium hydroxide inner salt (IX),
(3) 1-benzamido-8-cyano-3-ethyl-6-(o-chlorophenyl)-4H-s-triazolo[4,3-a][1,4]benzodiazepinium hydroxide inner salt (IX).

EXAMPLE 11

1-Benzenesulfonamido-8-chloro-3-methyl-6-phenyl-4H-s-triazolo[4,3-a][1,4]benzodiazepinium hydroxide inner salt (X)

To an ice cold stirred solution of 0.388 g. (0.0022 mole) of benzenesulfonyl chloride in 15 ml. of dried pyridine, 0.721 g. (0.002 mole) of 1-amino-8-chloro-3-methyl-6-phenyl-4H-s-triazolo[4,3-a][1,4]benzodiazepinium chloride (VI) is added. The resulting mixture is kept in an ice bath for about 15 hours and then allowed to warm to room temperature and stand for about 6 hours. It is then poured into cold, dilute aqueous sodium bicarbonate solution and extracted with chloroform. The extract is washed with brine, dried with sodium sulfate and concentrated. The residue is crystallized to give 1-benzenesulfonamido-8-chloro-3-methyl-6-phenyl-4H-s-triazolo[4,3-a][1,4]benzodiazepinium hydroxide inner salt (X).

Following the procedure of Example 11 but substituting other compounds of Formula VI and other alkyl (or aryl) sulfonyl halides, such as (1) 1-amino-9-chloro-6-(2,4-dimethoxyphenyl)-3-ethyl-4-methyl-4H-s-triazolo[4,3-a][1,4]benzodiazepinium bromide (VI) and methanesulfonyl chloride,
(2) 1-amino-8-fluoro-6-(3-methoxy-6-propylthiophenyl)-3-methyl-9-nitro-4H-s-triazolo[4,3-a][1,4]benzodiazepinium chloride (VI) and p-toluenesulfonyl bromide,
(3) 1-amino-9-bromo-3-ethyl-7-methoxy-6-(2-propoxy-4-trifluoromethylphenyl)-4H-s-triazolo[4,3-a][1,4]benzodiazepinium chloride (VI) and 1-naphthalenesulfonyl chloride, and the like, yields, respectively, (1) 9-chloro-6-(2,4-dimethoxyphenyl)-3-ethyl-1-methanesulfonamido-4-methyl-4H-s-triazolo[4,3-a][1,4]benzodiazepinium hydroxide inner salt (X),
(2) 8-fluoro-6-(3-methoxy-6-propylthiophenyl)-3-methyl-9-nitro-1-(p-toluenesulfonamido)-4H-s-triazolo[4,3-a][1,4]benzodiazepinium hydroxide inner salt (X), (3) 9-bromo-3-ethyl-7-methoxy-1-(1-naphthalenesulfonamido)-6-(2-propoxy-4-trifluoromethylphenyl)-4H-s-triazolo-[4,3-a][1,4]benzodiazepinium hydroxide inner salt (X), and the like.

EXAMPLE 12

1-Anilino-8-chloro-3-methyl-6-phenyl-4H-s-triazolo[4,3-a][1,4]benzodiazepinium hydroxide inner salt (XI)

A. A stirred mixture of 2.99 g. (0.01 mole) of 7-chloro-2-(1-methylhydrazino)-5-phenyl-3H-1,4-benzodiazepine (III), 3.12 ml. (0.022 mole) of triethylamine and 40 ml. of tetrahydrofuran is cooled in an ice bath and treated with a solution of phenylisocyanide dichloride (prepared as in Agew. Chem. Internat. Ed. 6, 649) in 20 ml. of tetrahydrofuran. The resulting mixture is allowed to warm slowly to room temperature and stand for about 18 hours. It is refluxed for about b 1 hour, cooled and concentrated to give 1-anilino-8-chloro-3-methyl-6-phenyl-4H-s-triazolo[4,3-a][1,4]benzodiazepinium chloride (VIII).

B. The residue containing 1-anilino-8-chloro-3-methyl-6-phenyl-4H-s-triazolo[4,3-a][1,4]benzodiazepinium chloride (VIII) (obtained in A, above) is mixed with cold, dilute aqueous sodium bicarbonate solution and extracted with chloroform. The extract is washed with brine, dried with sodium sulfate and concentrated. The residue is crystallized to give 1-anilino-8-chloro-3-methyl-6-phenyl-4H-s-triazolo-[4,3-a][1,4]benzodiazepinium hydroxide inner salt (XI).

Following the procedure of Example 12 but substituting other compounds of Formula III as starting materials, such as (1) 8-bromo-3-ethyl-5-(3-methoxy-5-propylphenyl)-2-(1-methylhydrazino)-3H-1,4-benzodiazepine (III),
(2) 5-(o-chlorophenyl)-2-(1-ethylhydrazino)-7-fluoro-3H-1,4-benzodiazepine (III),
(3) 6-chloro-8-cyano-3-propyl-2-(1-propylhydrazino)-5-(2-propylthio-5-trifluoromethylphenyl)-3H-1,4-benzodiazepine (III), and the like, yields, respectively,
(1) 1-anilino-9-bromo-4-ethyl-6-(3-methoxy-5-propylphenyl)-3-methyl-4H-s-triazolo[4,3-a][1,4]benzodiazepinium hydroxide inner salt (XI),
(2) 1-anilino-6-(o-chlorophenyl)-3-ethyl-8-fluoro-4H-s-triazolo[4,3-a][1,4]benzodiazepinium hydroxide inner salt (XI),
(3) 1-anilino-7-chloro-9-cyano-3,4-dipropyl-6-(2-propylthio-5-trifluoromethylphenyl)-4H-s-triazolo[4,3-a][1,4]benzodiazepinium hydroxide inner salt (XI), and the like.

EXAMPLE 13

7-Chloro-2,3-dihydro-2-(methylimino)-5-phenyl-1H-1,4-benzodiazepine-1-carbonitrile (XII)

A stirred solution of 1.5 g. (0.005 mole) of 7-chloro-2-(1-methylhydrazino)-5-phenyl-3H-1,4-benzodiazepine (III) and 3.7 g. (0.025mole) of triethyl orthoformate in 40 ml. of chloroform is treated with 1 g. of sulfuric acid and kept under nitrogen at room temperature for about 18 hours. The white crystalline product, 8-chloro-3-methyl-6-phenyl-4H-s-triazolo[4,3-a][1,4]benzodiazepinium hydrogen sulfate (VII), is collected by filtration, washed with chloroform and suspended in a mixture of chloroform and water. The mixture is neutralized with sodium bicarbonate and washed with chloroform. The aqueous layer is made strongly basic with 15% aqueous sodium hydroxide solution. The purple material that forms is extracted with chloroform. The extract is washed with brine, dried with potassium carbonate and concentrated under vacuum. (The chloroform extract is initially purple, but on standing, the color fades and becomes tan.) The residue is crystallized from a mixture of ethyl acetate and Skellysolve B to give 0.42 g. of 7-chloro-2,3-dihydro-2-(methylimino)-5-phenyl-1H-1,4-benzodiazepine-1-carbonitrile (XII), having a melting point of 184° to 190° C. (with decomposition). The analytical sample has a melting point of 186° to 188° C. (with decomposition); uv (EtOH) end absorption, λmax. 228 mµ (ε=31,000), 255 (shoulder 13,950), 277 (sh 5620), 305 (sh 2415). The ir, nmr and mass spectra support the structure proposed for the compound.

Anal. Calcd, for $C_{17}H_{13}ClN_4$: C, 66.13; H, 4.24; Cl, 11.48; N, 18.15. Found: C, 66.08; H, 4.27; Cl, 11.48; N, 18.08.

Following the procedure of Example 13 but substituting other compounds of Formula III as starting materials, such as (1) 6-bromo-3-methyl-2-(1-methylhydrazino)-5-(2-nitro-6-propoxyphenyl)-3H-1,4-benzodiazepine (III),
(2) 5-[2,4-di(ethylthio)phenyl]-7-ethoxy-2-(1-ethylhydrazino)-8-fluoro-3H-1,4-benzodiazepine (III),
(3) 7-chloro-9-cyano-3-ethyl-2-(1-propylhydrazino)-5-(3-propylthio-5-trifluoromethylphenyl)-3H-1,4-benzodiazepine (III), and the like, yields, respectively,
(1) 6-bromo-2,3-dihydro-3-methyl-2-(methylimino)-5-(2-nitro-6-propoxyphenyl)-1H-1,4-benzodiazepine-1-carbonitrile (XII),
(2) 5-[2,4-di(ethylthio)phenyl]-2,3-dihydro-7-ethoxy-2-(ethylimino)-8-fluoro-1H-1,4-benzodiazepine-1-carbonitrile (XII),
(3) 7-chloro-9-cyano-2,3-dihydro-3-ethyl-2-(propylimino)-5-(3-propylthio-5-trifluoromethylphenyl)-1H-1,4-benzodiazepine-1-carbonitrile (XII), and the like.

I claim:
1. An inner salt compound of the formula

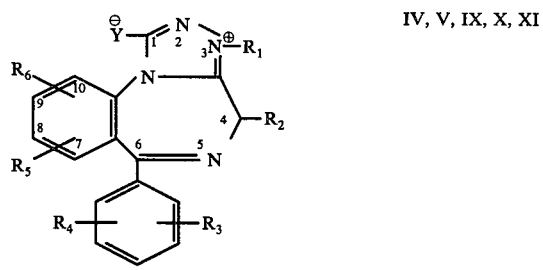

IV, V, IX, X, XI wherein Y is selected from the group consisting of hydroxy, mercapto and monosubstituted amino having an electronegative substituent selected from the group consisting of (1) arylamino wherein the aryl moiety is selected from the group consisting of phenyl and naphthyl, (2) alkanoylamino of 2 through 4 carbon atoms, (3) aroylamino wherein the aroyl moiety is selected from the group consisting of benzoyl and naphthoyl, (4) alkanesulfonamido of 1 through 3 carbon atoms and (5) arylsulfonamido wherein the aryl moiety is selected from the group consisting of phenyl and naphthyl; $R_1$ is lower alkyl of 1 through 3 carbon atoms; $R_2$ is selected from the group consisting of hydrogen and lower alkyl of 1 through 3 carbon atoms; R₃, R₄, R₅ and R₆ are selected from the group consisting of hydrogen, lower alkyl of 1 through 3 carbon atoms, halogen, nitro, trifluoromethyl, cyano, lower alkoxy of 1 through 3 carbon atoms and lower alkylthio of 1 through 3 carbon atoms, ⊖ appearing above Y indicates that the compound is an inner salt; ⊕ is the cation of the compound.

2. A compound of claim 1 wherein Y⊖ is mercapto, R₁ is methyl, R₂, R₃, R₄ and R₆ are hydrogen and R₅ is 8-chloro, namely, 8-chloro-1-mercapto-3-methyl-6-phenyl-4H-s-triazolo-[4,3-a][1,4]benzodiazepinium hydroxide inner salt.

3. A compound of claim 1 wherein Y⊖ is hydroxy, R₁ is methyl, R₂, R₄ and R₆ are hydrogen, R₃ is o-chloro and R₅ is 8-chloro, namely, 8-chloro-6-(o-chlorophenyl)-1-hydroxy-3-methyl-4H-s-triazolo[4,3-a][1,4]benzodiazepinium hydroxide inner salt.

4. A compound of claim 1 wherein Y⊖ is hydroxy, R₁ is methyl, R₂, R₃, R₄ and R₅ are hydrogen and R₅ is 8-chloro, namely, anhydro-b 8-chloro-1-hydroxy-3-methyl-6-phenyl-4H-s-traizolo[4,3-a][1,4]benzodiazepinium hydroxide.

5. A compound of the formula

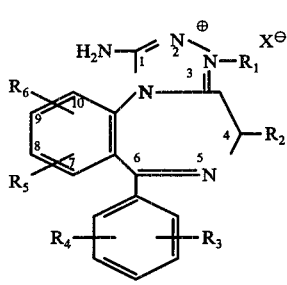

VI wherein R₁ is lower alkyl of 1 through 3 carbon atoms, R₂ is selected from the group consisting of hydrogen and lower alkyl of 1 through 3 carbon atoms, R₂, R₃, R₄, R₅ and R₆ are selected from the group consisting of hydrogen, lower alkyl of 1through 3 carbon atoms, halogen, nitro, trifluoromethyl, cyano, lower alkoxy of 1 through 3 carbon atoms and lower alkylthio of 1 through 3 carbon atoms, X⊖ is an anion derived from a pharmacologically acceptable acid addition salt and ⊕is the cation of the compound.

6. A compound of claim 5 wherein R₁ is methyl, R₂, R₃, R₄ and R₆ are hydrogen, R₅ is 8-chloro and X⊖ is chlorine, namely, 1-amino-8-chloro-3-methyl-6-phenyl-4H-s-triazolo[4,3-a][1,4]benzodiazepinium chloride.

7. A compound of the formula

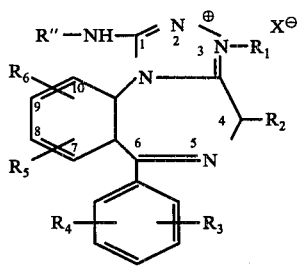

VII wherein R" is selected from the group consisting of lower alkyl of 1 through 3 carbon atoms, and phenyl and naphthyl, R₁ is lower alkyl of 1 through 3 carbon atoms, R₂, R₃, R₄, R₅ and R₆ are selected from the group consisting of hydrogen, lower alkyl of 1 through 3 carbon atoms, halogen, nitro, trifluoromethyl, cyano, lower alkoxy of 1 through 3 carbon atoms and lower alkylthio of 1 through 3 carbon atoms, X⊖ is an anion derived from a pharmacologically acceptable acid addition salt and ⊕ is the cation of the compound.

8. A compound of claim 7 wherein R" and R₁ are methyl, R₂, R₃, R₄ and R₆ are hydrogen, R₅ is 8-chloro and X⊖ is chlorine, namely, 8-chloro-3-methyl-1-methylamino-6-phenyl-4H-s-triazolo[4,3-a][1,4]benzodiazepinium chloride.

9. A compound of claim 7 wherein R" is phenyl, R₁ is methyl, R₂, R₃, R₄ and R₆ are hydrogen, R₅ is 8-chloro and X⊖ is chlorine, namely, 1-anilino-8-chloro-3-methyl-6-phenyl-4H-s-triazolo[4,3-a][1,4]benzodiazepinium chloride.

10. A compound of the formula

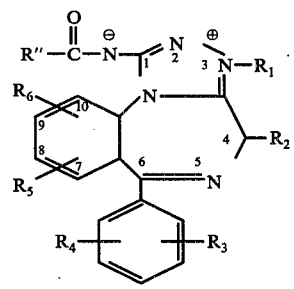

IX wherein R" is selected from the group consisting of lower alkyl of 2 through 4 carbon atoms, phenyl and naphthyl, R₁ is lower alkyl of 1 through 3 carbon atoms, R₂, R₃, R₄, R₅ and R₆ are selected from the group consisting of hydrogen, lower alkyl of 1 through 3 carbon atoms, halogen, nitro, trifluoromethyl, cyano, lowr alkoxy of 1 through 3 carbon atoms and lower alkylthio of 1 through 3 carbon atoms, ⊖ appearing above

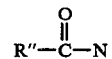

indicates that the compound is an inner salt and ⊕ is the cation of the compound.

11. A compound of claim 10 wherein R" and R₁ are methyl, R₂, R₃, R₄ and R₆ are hydrogen, R₅ is 8-chloro, namely 1-acetylamido-8-chloro-3-methyl-6-phenyl-4H-s-triazolo[4,3-a][1,4]benzodiazepinium hydroxide inner salt.

12. A compound of claim 10 wherein R" is phenyl, R₁ is methyl, R₂, R₃, R₄ and R₆ are hydrogen, R₅ is 8-chloro, namely, 1-benzamido-8-chloro-3-methyl-6-phenyl-4H-s-triazolo[4,3-a][1,4]benzodiazepinium hydroxide inner salt.

13. A compound of the formula

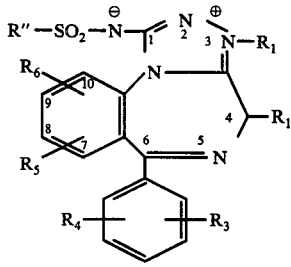

X

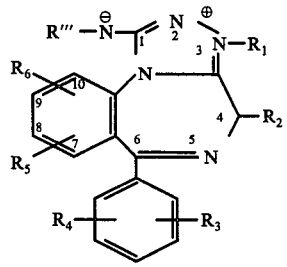

XI wherein R" is selected from the group consisting of lower alkyl of 1 through 3 carbon atoms, and phenyl and naphthyl, $R_1$ is lower alkyl of 1 through 3 carbon atoms, $R_2$, $R_3$, $R_4$, $R_5$ and $R_6$ are selected from the group consisting of hydrogen, lower alkyl of 1 through 3 carbon atoms, halogen, nitro, trifluoromethyl, cyano, lower alkoxy of 1 through 3 carbon atoms and lower alkylthio of 1 through 3 carbon atoms, ⊖ appearing above R"-SO$_2$-N indicates that the compound is an inner salt and ⊕ is the cation of the compound.

14. A compound of claim 13 wherein R" and $R_1$ are methyl, $R_2$, $R_3$, $R_4$ and $R_6$ are hydrogen, $R_5$ is 8-chloro, namely, 8-chloro-1-methanesulfonamido-3-methyl-6-phenyl-4H-s-triazolo[4,3-a][1,4]benzodiazepinium hydroxide inner salt.

15. A compound of claim 13 wherein R" is phenyl, $R_1$ is methyl, $R_2$, $R_3$, $R_4$ and $R_6$ are hydrogen, $R_5$ is 8-chloro, namely 1-benzenesulfonamido-8-chloro-3-methyl-6-phenyl-4H-s-triazolo[4,3-a][1,4]benzodiazepinium hydroxide inner salt.

16. A compound of the formula wherein R'" is selected from the group consisting of phenyl and naphthyl, $R_1$ is lower alkyl of 1 through 3 carbon atoms, $R_2$, $R_3$, $R_4$, $R_5$ and $R_6$ are selected from the group consisting of hydrogen, lower alkyl of 1 through 3 carbon atoms, halogen, nitro, trifluoromethyl, cyano, lower alkoxy of 1 through 3 carbon atoms and lower alkylthio of 1 through 3 carbon atoms, ⊖ appearing above R'"-N indicates that it is an anion and ⊕ is the cation of the compound.

17. A compound of claim 16 wherein R'" is phenyl, $R_1$ is methyl, $R_2$, $R_3$, $R_4$ and $R_6$ are hydrogen, $R_5$ is 8-chloro, namely, 1-anilino-8-chloro-3-methyl-6-phenyl-4H-s-triazolo[4,3-a][1,4]benzodiazepinium hydroxide inner salt.

* * * * *